(12) United States Patent
Liu et al.

(10) Patent No.: US 11,389,798 B2
(45) Date of Patent: Jul. 19, 2022

(54) DISEASE DIAGNOSTIC SYSTEM AND METHOD

(71) Applicant: CHARLES R. DREW UNIVERSITY OF MEDICINE AND SCIENCE, Los Angeles, CA (US)

(72) Inventors: Benjamin Liu, Los Angeles, CA (US); Eva McGhee, Los Angeles, CA (US); Robin Liu, Los Angeles, CA (US); Miguel Nava, Los Angeles, CA (US)

(73) Assignee: CHARLES R. DREW UNIVERSITY OF MEDICINE AND SCIENCE, Los Angeles, CA (US)

(*) Notice: Subject to any disclaimer, the term of this patent is extended or adjusted under 35 U.S.C. 154(b) by 512 days.

(21) Appl. No.: 16/359,589

(22) Filed: Mar. 20, 2019

(65) Prior Publication Data
US 2019/0291110 A1     Sep. 26, 2019

Related U.S. Application Data

(60) Provisional application No. 62/646,252, filed on Mar. 21, 2018.

(51) Int. Cl.
*C12Q 1/686* (2018.01)
*B01L 3/00* (2006.01)

(52) U.S. Cl.
CPC ..... *B01L 3/502761* (2013.01); *B01L 3/50273* (2013.01); *B01L 3/502738* (2013.01); *C12Q 1/686* (2013.01); *B01L 2200/027* (2013.01); *B01L 2200/0668* (2013.01); *B01L 2200/0684* (2013.01); *B01L 2400/0439* (2013.01)

(58) Field of Classification Search
CPC .............. C12Q 1/686; C12Q 2563/143; C12Q 2563/149; C12Q 2565/629; B01L 3/502761; B01L 3/50273; B01L 3/502738; B01L 2200/027; B01L 2200/0668; B01L 2200/0684; B01L 2400/0439
See application file for complete search history.

(56) References Cited

U.S. PATENT DOCUMENTS

| | | | |
|---|---|---|---|
| 6,664,104 B2 * | 12/2003 | Pourahmadi | C12M 47/06 422/547 |
| 9,096,823 B1 * | 8/2015 | Branch | B01L 3/5027 |
| 2008/0219894 A1 * | 9/2008 | Ganesan | G01N 1/4077 422/82.12 |
| 2016/0016171 A1 * | 1/2016 | Goel | B01L 3/5023 506/9 |

* cited by examiner

*Primary Examiner* — David C Thomas
(74) *Attorney, Agent, or Firm* — Pillsbury Winthrop Shaw Pittman LLP

(57) ABSTRACT

Infectious diseases have been sources of large-scale epidemics and pandemics resulting in millions of casualties worldwide. Detection of these biological agents normally involves several lab processes including sample preparation, nucleic acid separation and amplification, and diagnostic analysis. These steps, either performed manually or automated by high-throughput machinery, are tedious, expensive, and highly susceptible to cross-contamination. The present system is an integrated lab-on-a-device designed, developed, and tested in compatibility with a mechanical fixture for sample-to-answer biological analysis of infectious diseases.

20 Claims, 9 Drawing Sheets

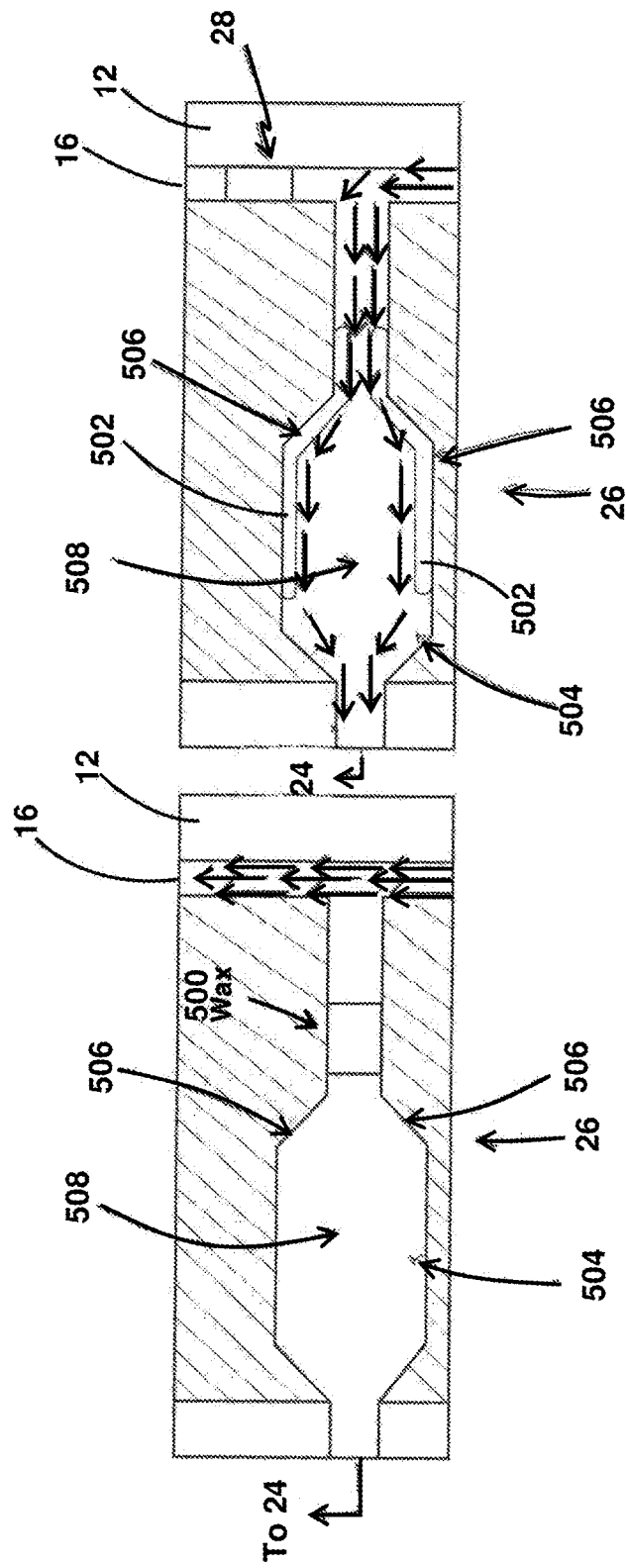

DISEASE DIAGNOSTIC SYSTEM AND METHOD

RELATED PATENT APPLICATIONS

This patent application claims the benefit of U.S. Provisional Patent Application No. 62/646,252 filed on Mar. 21, 2018, entitled DISEASE DIAGNOSTIC SYSTEM AND METHOD, naming Benjamin Liu, Eva McGhee, Robin Liu and Miguel Nava as inventors. The entire content of the foregoing application is incorporated herein by reference, including all text, tables and drawings.

BACKGROUND

1. Field

The present disclosure pertains to a system and method for performing a disease diagnostic using an integrated lab on a chip device.

2. Description of the Related Art

Infectious diseases have been sources of large-scale epidemics and pandemics resulting in millions of casualties worldwide. Detection of these biological agents normally involves several lab processes including sample preparation, nucleic acid separation and amplification, and diagnostic analysis. These steps, either performed manually or automated by high-throughput machinery, are tedious, expensive, and highly susceptible to cross-contamination.

SUMMARY

The following is a non-exhaustive listing of some aspects of the present techniques. These and other aspects are described in the following disclosure.

Accordingly, one or more aspects of the present disclosure relate to a disease diagnostic system. The system comprises a chip body, a mixing chamber, first, second, and third pumps, a main channel, a separation area, a waste chamber, an amplification chamber, first and second valves, and/or other components. The mixing chamber may be formed in the chip body. The mixing chamber may be configured to receive a biological sample for disease diagnosis. The mixing chamber may comprise magnetic beads, a cell lysis buffer, oligonucleotide binding receptors, and/or other components. The mixing chamber may be configured to receive energy to facilitate mixing in the mixing chamber to form a solution. The first pump may be formed in the chip body and coupled to the mixing chamber. The first pump may be configured to pump the solution out of the mixing chamber. The main channel may be formed in the chip body and coupled to the mixing chamber. The main channel may be configured to receive the solution pumped from the mixing chamber. The separation area may be formed in the main channel. The separation area may be configured to receive a magnet that traps bound ribonucleic acid (RNA) and/or deoxyribonucleic acid (DNA) molecules in the solution on a surface of the separation area. The waste chamber may be formed in the chip body and coupled to the main channel downstream from the separation area. The waste chamber may be configured to receive solution comprising unbound RNA and/or DNA molecules. The first valve may be positioned between the main channel and the waste chamber and configured to control flow of the solution without the bound RNA and/or DNA molecules through the main channel to the waste chamber. The amplification chamber may be formed in the chip body and coupled to the main channel downstream from the separation area. The amplification chamber may be configured to receive the bound RNA and/or DNA molecules for analysis. The second valve may be positioned between the main channel and the amplification chamber and configured to control flow of the bound RNA and/or DNA molecules through the main channel to the amplification chamber. The second pump may be formed in the chip body and coupled to the main channel. The second pump may be coupled to a cavity holding a wash buffer solution. The third pump may be formed in the chip body and coupled to the main channel. The third pump may be coupled to a cavity holding amplification solution.

With the first and second valves in a first configuration that allows flow through the main channel to the waste chamber and blocks flow to the amplification chamber, and with the bound RNA and/or DNA molecules trapped in the separation area, activation of the second pump pumps the wash buffer solution and the solution comprising the unbound RNA and/or DNA molecules through the main channel into the waste chamber. With the first and second valves in a second configuration that allows flow through the main channel to the amplification chamber and blocks flow to the waste chamber, and with the bound RNA and/or DNA molecules released from the separation area, actuation of the third pump pumps the amplification solution and the bound RNA and/or DNA molecules through the main channel into the amplification chamber.

In some embodiments, the mixing chamber comprises one or more cavities configured to trap air bubbles when fluid is loaded into the mixing chamber. The air bubbles may be configured to function as mechanical actuators during mixing in the mixing chamber. In some embodiments, the mixing chamber may be configured to receive external energy from a piezoelectric transducer (PZT) such that vibrations are transferred from the PZT to the mixing chamber and cause the air bubbles to oscillate and produce acoustic incident waves in the mixing chamber to cause the RNA and/or DNA molecules to couple with the magnetic beads. In some embodiments, the first pump comprises an electrochemical decomposition reaction (electrolysis) of water in a sodium chloride solution. In some embodiments, the second pump comprises a first blister formed in the chip body. The first blister may be configured to be actuated by a first mechanical external force. In some embodiments, the third pump comprises a second blister formed in the chip body. The second blister may be configured to be actuated by a second mechanical external force. In some embodiments, the first valve and the second valve may be wax valves. In some embodiments, the first valve and the second valve may be actuated by one or more heat sources coupled to a surface of the chip body at or near the first valve and the second valve. In some embodiments, the amplification chamber is configured to facilitate, for RNA molecules: amplification using transcription-mediated amplification; and analysis for fluorescent signals with a real-time polymerase chain reaction. In some embodiments, the system further comprises an external fixture configured to: receive the chip body and removably couple with the chip body to retain the chip body in a predetermined orientation with respect to the external fixture; actuate the PZT; activate the first pump; trap and untrap the bound RNA and/or DNA molecules; actuate the first and second valves to cause the system to change from the first configuration to the second configuration, and actuate the second and third pumps.

Further, one or more aspects of the present disclosure relate to a disease diagnosis method performed with a diagnostic system. The system comprises a chip body, a mixing chamber, first, second, and third pumps, a main channel, a separation area, a waste chamber, an amplification chamber, first and second valves, and/or other components. The method comprises forming the mixing chamber in the chip body. The mixing chamber may be configured to receive a biological sample for disease diagnosis. The mixing chamber may comprise magnetic beads, a cell lysis buffer, oligonucleotide binding receptors, and/or other components. The mixing chamber may receive energy to facilitate mixing in the mixing chamber to form a solution. The method comprises forming the first pump in the chip body, coupling the first pump to the mixing chamber, and pumping the solution out of the mixing chamber with the first pump. The method comprises forming the main channel in the chip body, coupling the main channel to the mixing chamber, and receiving the solution pumped from the mixing chamber with the main channel. The method comprises forming the separation area in the main channel and receiving a magnet that traps bound RNA and/or DNA molecules in the solution on a surface of the separation area. The method comprises forming the waste chamber in the chip body, coupling the waste chamber to the main channel downstream from the separation area, and receiving solution comprising unbound RNA molecules with the waste chamber. The method comprises positioning the first valve between the main channel and the waste chamber to control flow of the solution comprising the unbound RNA and/or DNA molecules through the main channel to the waste chamber. The method comprises forming the amplification chamber in the chip body, coupling the amplification chamber to the main channel downstream from the separation area, and receiving the bound RNA and/or DNA molecules for analysis with the amplification chamber. The method comprises positioning the second valve between the main channel and the amplification chamber to control flow of the bound RNA and/or RNA molecules through the main channel to the amplification chamber. The method comprises forming the second pump in the chip body and coupling the second pump to the main channel and a cavity holding a wash buffer solution. The method comprises forming the third pump in the chip body and coupling the third pump to the main channel and a cavity holding amplification solution. The method comprises, with the first and second valves in a first configuration that allows flow through the main channel to the waste chamber and blocks flow to the amplification chamber, and with the bound RNA and/or DNA molecules trapped in the separation area, actuating the second pump to pump the wash buffer solution and the solution comprising the unbound RNA and/or DNA molecules through the main channel into the waste chamber. The method comprises, with the first and second valves in a second configuration that allows flow through the main channel to the amplification chamber and blocks flow to the waste chamber, and with the bound RNA and/or DNA molecules released from the separation area, actuating the third pump to pump the amplification solution and the bound RNA and/or DNA molecules through the main channel into the amplification chamber.

In some embodiments, the mixing chamber further comprises one or more cavities configured to trap air bubbles when fluid is loaded into the mixing chamber. The air bubbles may be configured to function as mechanical actuators during mixing in the mixing chamber. In some embodiments, the method further comprises receiving, with the mixing chamber, external energy from a PZT such that vibrations are transferred from the PZT to the mixing chamber and cause the air bubbles to oscillate and produce acoustic incident waves in the mixing chamber to cause the RNA and/or DNA molecules to couple with the magnetic beads. In some embodiments, the first pump comprises an electrochemical decomposition reaction (electrolysis) of water in a sodium chloride solution. In some embodiments, the second pump comprises a first blister formed in the chip body, the method further comprising actuating the first blister with a first mechanical external force. In some embodiments, the third pump comprises a second blister formed in the chip body. The method further comprises actuating the second blister with a second mechanical external force. In some embodiments, the first valve and the second valve are wax valves. In some embodiments, the method further comprises actuating the first valve and the second valve with one or more heat sources coupled to a surface of the chip body at or near the first valve and the second valve. In some embodiments, the method further comprises facilitating, with the amplification chamber, for RNA molecules: amplification using transcription-mediated amplification; and analysis for fluorescent signals with a real-time polymerase chain reaction. In some embodiments, the system further comprises an external fixture. The method further comprises: receiving, with the external fixture, the chip body and removably coupling with the chip body to retain the chip body in a predetermined orientation with respect to the external fixture; actuating, with the external fixture, the PZT; activating, with the external fixture, the first pump; trapping and untrapping, with the external fixture, the bound RNA and/or DNA molecules; actuating, with the external fixture, the first and second valves to cause the system to change from the first configuration to the second configuration, and actuating, with the external fixture, the second and third pumps.

These and other objects, features, and characteristics of the system or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The above-mentioned aspects and other aspects of the present techniques will be better understood when the present application is read in view of the following figures in which like numbers indicate similar or identical elements.

FIG. 5A illustrates a valve in a closed position.

FIG. 5B illustrates the valve in an open position.

Figure 1:
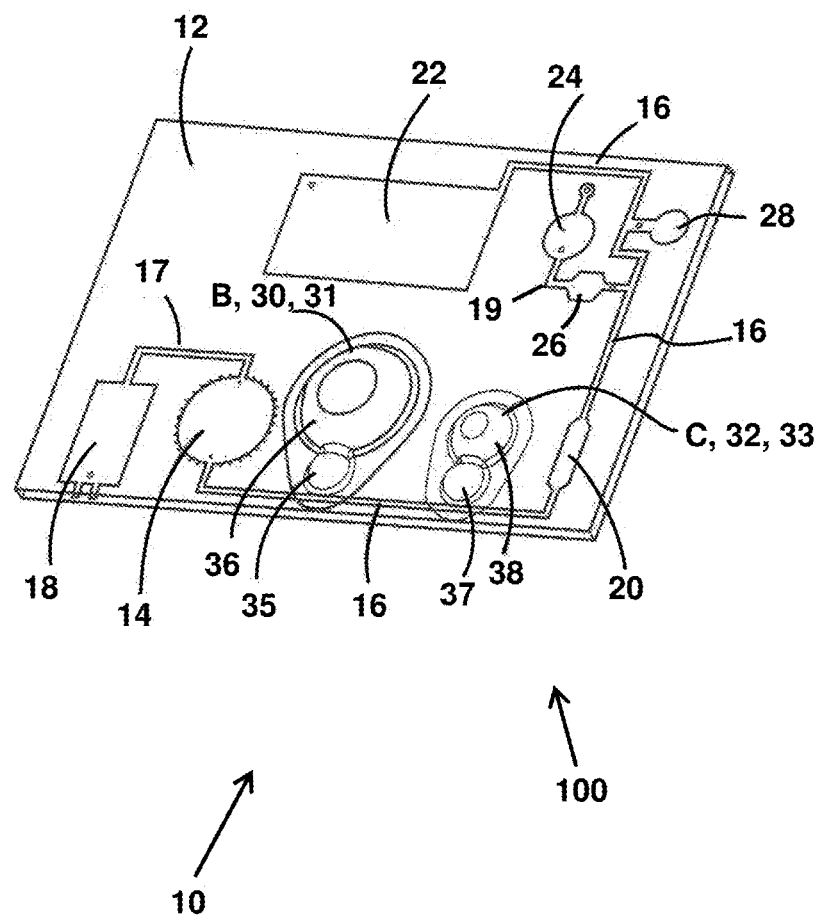
FIG. 1 is a schematic illustration of one embodiment of the present disease diagnostic system.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF EXEMPLARY EMBODIMENTS

To mitigate the problems described herein, the inventors had to both invent solutions and, in some cases just as importantly, recognize problems overlooked (or not yet foreseen) by others in the field of buying and selling shares or other securities. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

The present disease diagnostic system integrates at least four traditionally non-integrated components. These components include 1) acoustic-based micromixers that perform the sample preparation process and enhance mixing between biological sample targets and magnetic beads for RNA separation; 2) reagent-storing blisters for the storage of solutions and simplification of a microchannel to a one-pump flow system; 3) an electrochemical pump to control fluidic movement; and 4) an integrative fixture that facilitates mechanical operation of the reagent-storing blisters and a stabilizing platform for device operation. The present system integrates the (e.g., infectious) disease diagnostic process into a handheld diagnostic system configured for the diagnosis of thousands of RNA-based (infectious) diseases. While infection rates continue to increase and cost health care systems billions of dollars annually, there are currently few options available to prevent the increasing incidence of infections. Until now, testing capabilities that are noninvasive and that are applicable to various venues (e.g., in a hospital, in rural areas, etc.) were a particular challenge for the diagnosis of these infections.

Many current microfluidic or microarray devices pursue single function optimization and use purified DNA or homogeneous samples as input samples. However, practical applications in clinical and environmental analysis require processing of samples as complex and heterogeneous as whole blood or contaminated environmental fluids. With a lack of practical versatility and integration of diagnostic components for effective sample-to-answer biological analysis, current microfluidic lab on a chip (LOC) devices cannot be fully integrated for rapid diagnostic applications.

Figure 2:
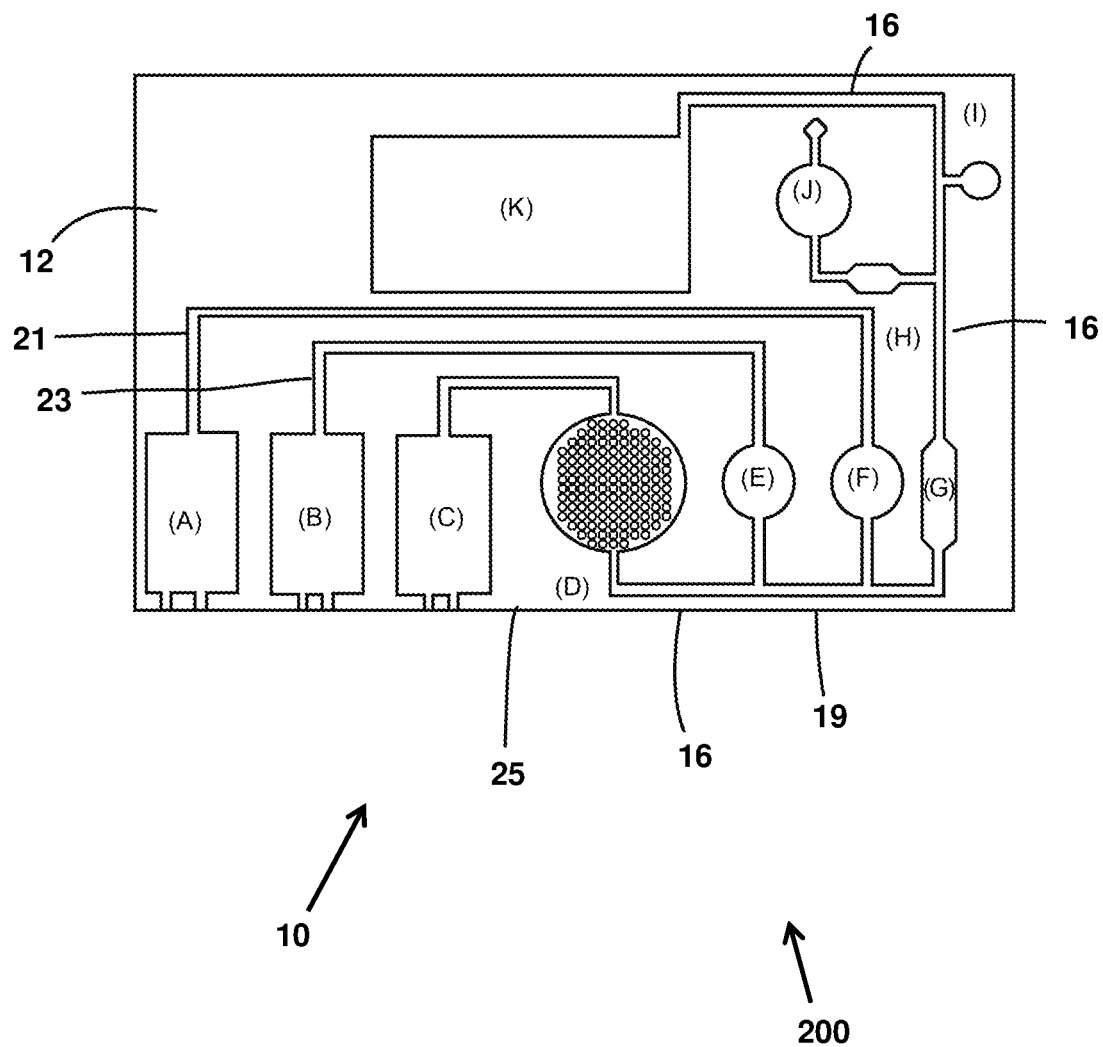
FIG. 2 is a schematic of another embodiment of the present disease diagnostic system.

FIG. 1 is a schematic illustration of one embodiment 100 of the present disease diagnostic system 10. FIG. 2 is a schematic of another embodiment 200 of the present disease diagnostic system 10. As shown in FIGS. 1 and/or 2, the system 10 may comprise a chip body 12, a mixing chamber 14 (FIG. 1) or D (FIG. 2), a main channel 16, a first pump 18 (FIG. 1) or A (FIG. 2), a separation area 20 (FIG. 1) or G (FIG. 2), a waste chamber 22 (FIG. 1) or K (FIG. 2), an amplification chamber 24 (FIG. 1) or J (FIG. 2), first and second valves 26 and 28 (FIG. 1) or H and I (FIG. 2), a second pump B, a third pump C, and/or other components.

The chip body 12 may be a unitary structure having a substantially planar appearance and/or other appearances. The chip body 12 may include various biological sample processing features (e.g., as described herein). In some embodiments, the chip body 12 may be and/or include a "lab-on-a-chip" (LOC) device. In some embodiments, the chip body 12 may be a silicon-based chip. In some embodiments, the chip body 12 may be formed with one or more of the components described herein using silicon processing techniques. In some embodiments, the silicon processing techniques may be similar to and/or the same as the silicon processing techniques in computer microchip industry applications for fabrication of devices configured to miniaturize mechanical environmental sensing and/or processing operations and/or other operations. The chip body 12 is configured such that various laboratory functions involving complex machinery and procedures are synthesized and integrated into a single microfluidic platform (e.g., the disease diagnostic system 10 described herein). The chip body 12 may be configured for designated medical purposes and/or other purposes. For example, the chip body 12 may be configured to facilitate the performance of individual functions involved in a diagnostic process including sample preparation, mixing steps, chemical reactions, detection operations, and/or other operations.

Rapid, consistent, micro mixing of liquid solutions is challenging in microfluidic systems. Because microfluidic environments generally inherit fluidic properties in which viscous forces within the fluid dominate inertial forces, mixing is dominated by pure molecular diffusion. Turbulent-driven macromixing enhancements that have been used in macro-scale fluidic environments are not practically attainable in micro-scale systems. Pure diffusion-based mixing processes are highly inefficient in that they take several hours to complete. This is true for solutions containing macromolecules (e.g., RNA) or large particles (e.g., magnetic capture beads), in which low diffusion coefficients complicate mixing efficiencies with greater effect.

The mixing chamber 14 (FIG. 1) or D (FIG. 2) may be formed in and/or by the chip body 12. The mixing chamber 14, D may facilitate rapid, consistent micromixing of liquid solutions and/or other materials. The mixing chamber 14, D may be configured to receive a biological sample for disease diagnosis and/or other materials. The mixing chamber 14, D may comprise magnetic beads, a cell lysis buffer, oligonucleotide binding receptors, and/or other components. The mixing chamber 14, D may be configured to receive energy to facilitate mixing in the mixing chamber 14, D to form a solution. In some embodiments, the mixing chamber 14, D comprises one or more cavities configured to trap air bubbles when fluid is loaded into the mixing chamber 14, D.

The air bubbles may be configured to function as mechanical actuators during mixing in the mixing chamber 14, D. In some embodiments, the mixing chamber 14, D may be configured to receive external energy from a piezoelectric transducer (PZT) such that vibrations are transferred from the PZT to the mixing chamber 14, D and cause the air bubbles to oscillate and produce acoustic incident waves in the mixing chamber to cause the RNA and/or DNA molecules to couple with the magnetic beads. In some embodiments, the interaction of these waves in individual acoustic fields influences the formation of acoustic standing waves and global convective currents. The propagation of these acoustic waves may enhance the sample preparation process, as cell lysis buffer mixes with cells, releasing RNA and/or RNA targets. These RNA and/or DNA targets may then be bound to the complimentary oligonucleotide receptors and attached magnetic beads for future magnetic separation. In some embodiments, the mixing chamber 14, D may be configured to facilitate performing the sample mixing process in under 10 seconds. In some embodiments, the mixing chamber 14, D may be configured to facilitate performing the sample mixing process in under 7 seconds. In some embodiments, the mixing chamber 14, D may be configured to facilitate performing the sample mixing process in under 5 seconds.

In some embodiments, this acoustic-enhanced micromixing is based on the use of acoustic energy resonating in air interfaces to manipulate particle motion through acoustic incident waves, and in turn, enhance mixing of self contained solutions (e.g., within the mixing chamber). In some embodiments, acoustic energy created by a function generator may be transferred into a PZT disk which spreads acoustic vibrations (e.g., at controlled frequency) to the mixing chamber 14, D. Within the lateral cavities and small air pockets, fluid surface tension traps air within the pockets. When exposed to acoustic vibrations, these air bubbles vibrate rapidly. At the resonance frequency, these air bubble interfaces may produce acoustic incident waves. The mixing chamber 14, D is configured to produce close proximity between pockets for rapid reflection of waves.

Micropumps are important components in integrated microfluidic devices, in that they control transportation of fluids to designated locations. Micropumps can be classified in two main categories based on different actuation mechanisms and sources. These main groups of pumps are membrane-actuated (mechanical) and non-membrane actuated. Membrane-actuated pumps are further divided into source-driven subtypes including piezoelectric, electrostatic, thermopneumatic, etc. The pressure-driven pump mechanisms have respective drawbacks including complicated design and fabrication procedures, high costs, and intricate operation. Non-membrane pumping relies on electro-hydrodynamics, electro-osmosis, diffusion, traveling waves, etc. An effective combination of convenient cost, performance, operation, and design/fabrication does not exist for several applications. An effective micropump that meets these requirements, such as the combination of pumps described herein, simplifies existing pumping procedures for more cost-effective biological sample-to-answer chip analysis.

The first pump 18 (FIG. 1) or A (FIG. 2) may be formed in the chip body 12 and coupled to the mixing chamber 14, D. In some embodiments, the first pump 18, A may be a micropump and/or other pumps. The first pump 18, A may be configured to pump the solution out of the mixing chamber 14, D and/or control other solution flow in the system. In some embodiments, the first pump 18, A may be a membrane-actuated (mechanical) pump, a non-membrane actuated pump, and/or other pumps. In some embodiments, the first pump 18, A may be a piezoelectric pump, an electrostatic pump, a thermopneumatic pump, and/or other pumps. In some embodiments, the first pump 18, A may rely on electro-hydrodynamics, electro-osmosis, diffusion, traveling waves, and/or other operations. In some embodiments, the first pump 18, A comprises an electrochemical decomposition reaction (electrolysis) of water in a sodium chloride solution.

In some embodiments, at an anode of the first pump 18, A, the oxidation of chlorine occurs rather than the oxidation of water since the over potential for the oxidation of sodium chloride to chlorine is lower than the over potential for the oxidation of water to oxygen. In some embodiments, the use of sodium chloride may suppress oxygen gas production, effectively regulate pumping functions, and eliminate safety risks associated with electrolysis-based pumping. In some embodiments, the hydroxide ions and dissolved chlorine gas react further to form hypochlorous acid. The application of DC current to the sodium chloride solution may instigate a decomposition reaction, creating two oppositely charged poles, the anode and cathode. This separation of the ionic bonds leads to production of new chemical compounds and molecules including hydrogen gas for pumping and sodium hypochlorite.

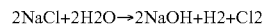

$$2NaCl+2H_2O \rightarrow 2NaOH+H_2+Cl_2$$

The equation above describes the chemical reaction that may take place. Oxidation takes place at the anode (oxygen and chlorine ions), while reduction takes place at the cathode (release of hydrogen gas). The separation of ionic compounds creates further chemical activity with resulting molecule exposures (i.e. chlorine and sodium hydroxide ions—see discussion of FIGS. 7A and 7B below).

The main channel 16 may be formed in the chip body 12 and coupled to the mixing chamber 14, D and/or other components. The main channel 16 may be configured to receive the solution pumped from the mixing chamber 14, D. In some embodiments, the main channel 16 (and/or other channels 17 (FIG. 1), 19 (FIG. 1), 21 (FIG. 2), 23 (FIG. 2), 25 (FIG. 2) shown in FIGS. 1 and 2 for example) may be about 0.88 mm in depth and about 1 mm in width. However, this is not intended to be limiting. Many other channel dimensions are possible. The main channel 16 and/or other microchannels of the present system 10 may have any dimensions and/or shapes that allow the system 10 to function as described herein.

Magnetic separation techniques are used in system 10. System 10 may rely on inherent negative charges in biological materials, the attachment of magnetic antibodies to these materials, of which contain one-sided oligonucleotide strands and one-sided magnetic beads, and/or other factors. For example, system 10 may utilize these techniques for the separation of RNA target molecules using similar oligonucleotide, magnetic bead particles.

The separation area 20 (FIG. 1) or G (FIG. 2) may be formed in the main channel 16. The separation area 20, G may be configured to receive a magnet that traps bound ribonucleic acid (RNA) and/or deoxyribonucleic acid (DNA) molecules in the solution on a surface of the separation area 20, G.

The waste chamber 22 (FIG. 1) or K (FIG. 2) may be formed in the chip body 12 and coupled to the main channel 16 downstream from the separation area 20, G. The waste chamber 22, K may be configured to receive the solution without the bound RNA and/or DNA molecules and/or other materials.

Microvalves are also integral components in system 10, facilitating separation of fluids and transportation of targets into specific areas. There are two main categories of microvalves including passive microvalves (without actuation) and active microvalves (with actuation). Passive valves are generally facilitate fluid flow in one direction. Active microvalves couple an intricate, flexible channel membrane to an electromechanical actuator to regulate valve opening and closing based on thermo-pneumatic, bimetallic, shape-memory, electrostatic, piezoelectric, or electromagnetic principles.

The first valve 28 (FIG. 1) or I (FIG. 2) may be positioned between the main channel 16 and the waste chamber 22, K and configured to control flow of the solution without the bound RNA and/or DNA molecules through the main channel 16 to the waste chamber 22 or K.

The amplification chamber 24 (FIG. 1) or J (FIG. 2) may be formed in the chip body 12 and coupled to the main channel 16 downstream from the separation area 20, G. The amplification chamber 24, J may be configured to receive the bound RNA and/or DNA molecules for analysis and/or other materials. In some embodiments, for RNA molecules, the amplification chamber 24, J is configured to facilitate: amplification using transcription-mediated amplification; and analysis for fluorescent signals with a real-time polymerase chain reaction. In some embodiments, the amplification chamber 24, J and/or other components of the system 10 may be configured to facilitate CT assays carried out in the integrated device based on transcription mediated amplification (as described above). During this process, reverse transcriptase, using a bound T7 primer creates a complimentary DNA strand to its original RNA target, erases the original RNA strand, and copies the resulting DNA strand to form a cDNA double-strand, that serves as a template for RNA amplification. T7 RNA transcriptase initiates transcription on the cDNA template, creating several hundreds of copies of RNA amplicons. Single-stranded nucleic acid torches with fluorophores and quenchers bind to the RNA amplicons, and through excitement, fluoresce, creating a signal to display fluorescent intensity. The generated fluorescent intensity is measured in representation of RNA targets captured and amplified. Intensity directly corresponds to level of target capturing.

The second valve 26 (FIG. 1) or H (FIG. 2) may be positioned between the main channel 16 and the amplification chamber 24, J and configured to control flow of bound RNA and/or DNA molecules through the main channel 16 to the amplification chamber 24, J.

In some embodiments, the first valve 28, I and/or the second valve 26, H may be a microvalve configured to separate fluids and/or transport of targets into specific areas of the chip body 12. In some embodiments, such microvalves may include passive microvalves (e.g., without actuation), active microvalves (e.g., with actuation), and/or other microvalves. In some embodiments, passive valves generally facilitate fluid flow in one direction. In some embodiments, active valves may open and close fluid passages for fluid distribution into designated areas in the chip body. In some embodiments, a microvalve may couple an intricate, flexible channel membrane to an electromechanical actuator to regulate valve opening and closing based on thermo-pneumatic, bimetallic, shape-memory, electrostatic, piezoelectric, electromagnetic, and/or other principles. In some embodiments, the first valve 28, I and the second valve 26, H may be wax valves. In some embodiments, the first valve 28, I and the second valve 26, H may be actuated by one or more heat sources coupled to and/or otherwise in contact with one or more surfaces of the chip body 12 at or near the first valve 28, I and/or the second valve 26, H.

In some embodiments, the first (28, I) and second (26, H) valves may be one-shot valves. For example, the second valve 26, H may be a normally closed valve and the first valve 28, I may be a normally open valve. The first (28, I) and second (26, H) valves may rely on changes of wax in physical states to open and close channels leading to the waste chamber 22, K (e.g., a portion of main channel 16) and/or the amplification chamber 24, J (e.g., a channel 19). With temperature controlled by a resistive heater (e.g., that is part of the external fixture described below), the wax of the first and/or second valves may act as an actuator in the valving process.

Reagent-storing blisters create desirable storing conditions for enzymes and other sensitive biochemicals, and are integratable components for system 10. In some embodiments (e.g., as described below), system 10 includes one-compression-based blisters. In some embodiments, these blisters may include attachable (e.g., to chip body 12) blister components. In some embodiments, on the bottom of the blisters, a sharp module is positioned for the cracking of a seal, and opening of stored reagents to the main channel 16.

The second pump B may be formed in the chip body 12 and coupled to the main channel 16 (e.g., or in some embodiments via channel 23 shown in FIG. 2). The second pump B may be coupled to a cavity 30 (FIG. 1) or E (FIG. 2) holding a wash buffer solution. In some embodiments, the second pump B may be a micropump and/or other pumps. In some embodiments, the second pump B may be a membrane-actuated (mechanical) pump, a non-membrane actuated pump, and/or other pumps. In some embodiments, the second pump B may be a piezoelectric pump, an electrostatic pump, a thermopneumatic pump, and/or other pumps. In some embodiments, the second pump B may rely on electro-hydrodynamics, electro-osmosis, diffusion, traveling waves, and/or other operations. In some embodiments, the second pump B comprises a first blister 31 (FIG. 1) formed in the chip body 12. The first blister 31 may be configured to be actuated by a first mechanical external force. For example, this mechanical external force may be provided by a separate device and/or fixture configured to press on the blister 31, a person pressing on the blister 31, and/or be provided in other ways.

The third pump may C be formed in the chip body 12 and coupled to the main channel 16 (e.g., or in some embodiments via channel 25 shown in FIG. 2). The third pump C may be coupled to a cavity 32 (FIG. 1) or F (FIG. 2) holding amplification solution. In some embodiments, the third pump C may be a micropump and/or other pumps. In some embodiments, the third pump C may be a membrane-actuated (mechanical) pump, a non-membrane actuated pump, and/or other pumps. In some embodiments, the third pump C may be a piezoelectric pump, an electrostatic pump, a thermopneumatic pump, and/or other pumps. In some embodiments, the third pump C may rely on electro-hydrodynamics, electro-osmosis, diffusion, traveling waves, and/or other operations. In some embodiments, the third pump C comprises a second blister 33 (FIG. 1) formed in the chip body 12. The second blister 33 may be configured to be actuated by a second mechanical external force. For example, this mechanical external force may be provided by a separate device and/or fixture configured to press on the blister 33, a person pressing on the blister 33, and/or be provided in other ways.

In some embodiments, the first and second blisters 31 and 33 and/or cavities E and F may be and/or include reagent-storing blisters and/or cavities configured to store enzymes, wash buffer solution, amplification solution, and/or other materials. In some embodiments, the first and/or second blisters 31 and 33 and/or cavities E and F may be and/or include a one-compression-based blister and/or cavity which incorporates attachable blister components. For example, such blisters, may include a sharp module positioned for the cracking a blister seal, and opening stored reagents to the main channel. In some embodiments, the reagent-storing blisters 31 and 33 and/or cavities E and F incorporate two main blister subsections. A smaller section 35 and 37 (FIG. 1) may be configured to control the initial opening of the blister for the initiation of pumping and a larger section 36 and 38 may control the mechanical pumping of the solution through the main channel 16. In such embodiments, a lead and/or other metal and/or non-metal ball may be placed in (e.g., the center of) the smaller section 35 and 37 of the reagent-storing blisters. When the section is compressed, the blister surface contacts the ball, opening the blister contents to the main channel by opening the seal. After the opening of the blister, the larger section 36 and 38 of the blisters may be compressed, creating a controlled mechanism to pump the stored solution into the main channel 16 until maximum compression is reached.

In some embodiments, the first and second blisters 31 and 33 are configured to control fluid flow, cross contamination, and retraction and/or pumping of fluid. Controlling these elements may allow for reagent storage, pumping, and/or operations such as shuttle mixing.

With the first and second valves 28 and 26 or I and H in a first configuration that allows flow through the main channel 16 to the waste chamber 22, K and blocks flow to the amplification chamber 24, J, and with the bound RNA and/or DNA molecules trapped in the separation area 20, G, activation of the second pump B, pumps the wash buffer solution and the solution comprising unbound RNA and/or DNA molecules through the main channel 16 into the waste chamber 22, K. In some embodiments, as the wash buffer solution flows through the magnetic separation center 20, G, it removes extraneous particles from the channel surface and purifies the captured RNA and/or DNA molecules. With the first and second valves 28 and 26 or I and H in a second configuration that allows flow through the main channel 16 to the amplification chamber 24, J, and blocks flow to the waste chamber 22, K, and with the bound RNA and/or DNA molecules released from the separation area 20, G, actuation of the third pump C pumps the amplification solution and the bound RNA and/or DNA molecules through the main channel 16 into the amplification chamber 24, J. For example, after RNA and/or DNA purification, a heating process enacted by an adhesive heater takes place, closing the first (e.g., waste) valve 28, I and opening the second (e.g., amplification) valve 24, J for the transfer of separated RNA and/or DNA molecules into the amplification chamber 24, J for analysis. The second reagent-storing blister 33 (e.g., the third pump C) is then mechanically compressed, causing the amplification solution to flow through the magnetic separation center 20, G (carrying the bound RNA and/or DNA molecules) and into the amplification chamber 24, J. At this stage, the magnet used for separation would be removed. The obtained sample is then amplified, for RNA molecules, using transcription-mediated amplification and analyzed for fluorescent signals under a real-time PCR reader for diagnostic results (e.g., as described above).

Figure 3:
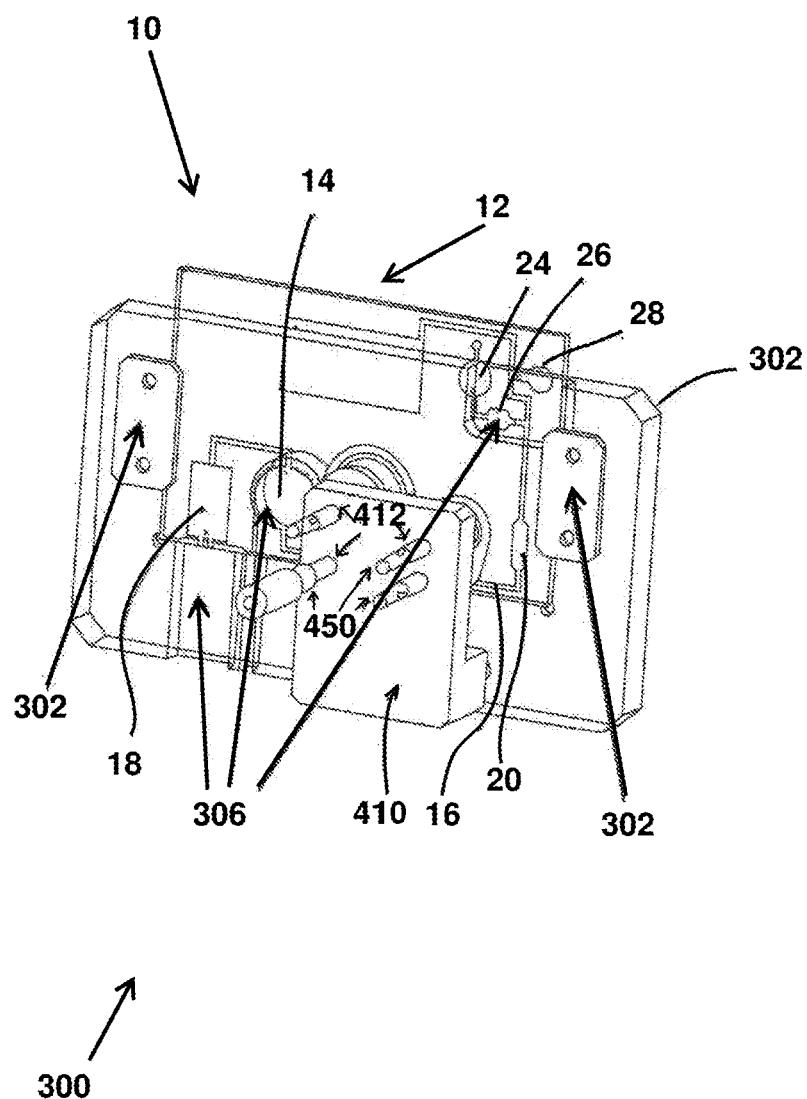
FIG. 3 illustrates a first portion of an external fixture.
Figure 4:
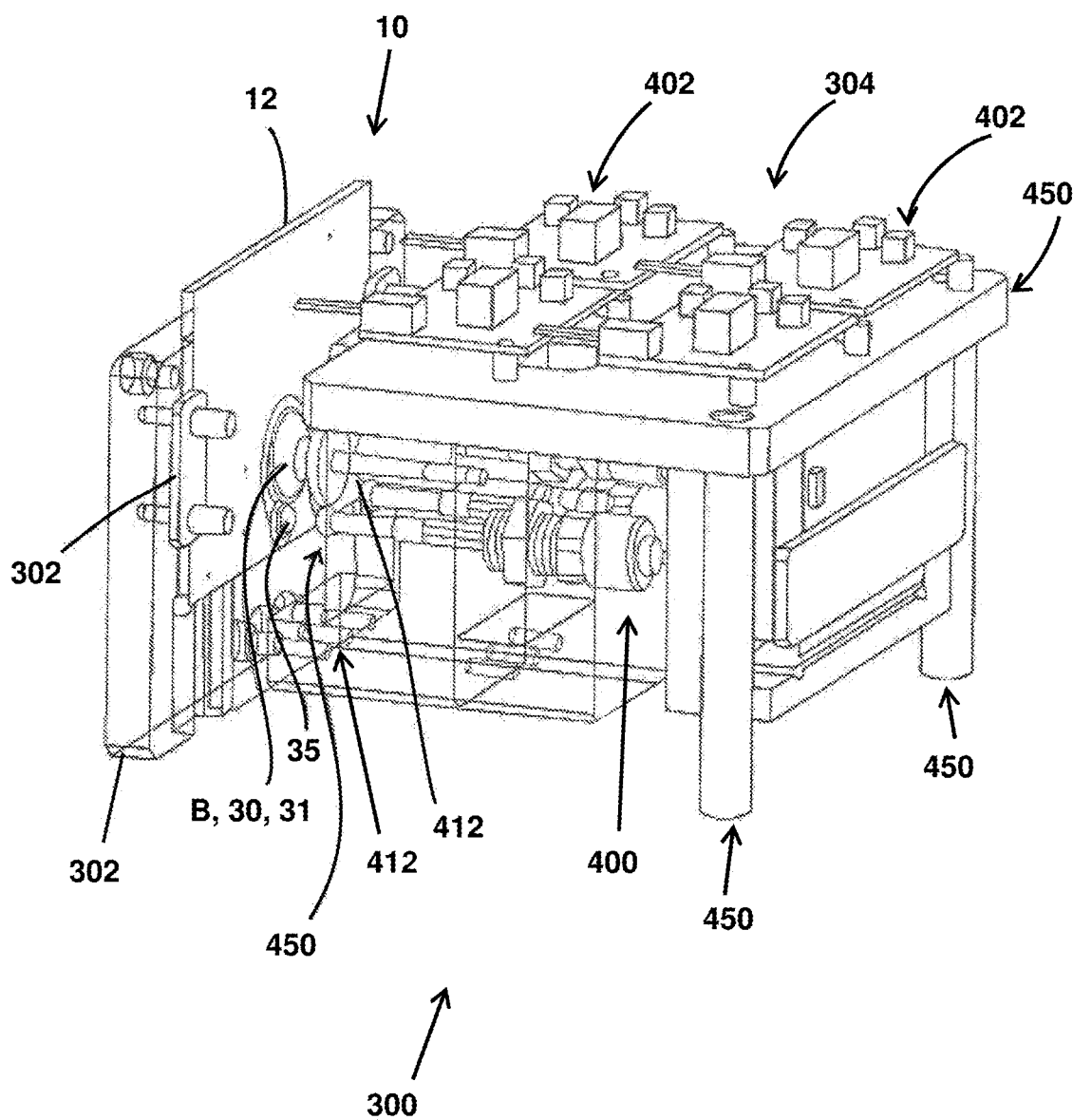
FIG. 4 illustrates a second portion of the external fixture.

In some embodiments, the system 10 further comprises an external fixture. FIG. 3 and FIG. 4 illustrate portions 302 and 304 (FIG. 4) the external fixture 300. Portion 302 may be configured to receive chip body 12. Portion 302 may removably couple with chip body 12 and include recessed and/or hollow portions 306 configured to permit access to various components (e.g., a pump, the mixing chamber, the amplification chamber, etc.) of chip body 12. Portion 304 may be configured to receive chip body 12 and portion 302 (e.g., as shown in FIG. 4). The external fixture 300 is configured to: receive the chip body 12 and removably couple (e.g., via coupling components 302 such as clips, clamps, nuts, bolts, screws, adhesive, slots, channels, and/or other coupling components) with the chip body 12 to retain the chip body 12 in a predetermined orientation with respect to the external fixture 300; actuate the PZT; activate the first pump 18, A (FIGS. 1 and 2); trap and untrap the bound RNA and/or DNA molecules; actuate the first and second valves 28 and 26 or I and H (FIGS. 1 and 2) to cause the system 10 to change from the first configuration to the second configuration, and actuate the second and third pumps B and C (FIGS. 1 and 2). In some embodiments, the external fixture may 300 be coupled to and/or include motors 400 (FIG. 4) for mechanical pump operation, one or more printed circuit board (PCB) controllers 402 (FIG. 4) configured to control and/or automate pump settings and operations, and/or other components. In some embodiments, the external fixture includes other components 410 (e.g., moveable pins 412, posts, etc.) for the mechanical operation of the disease diagnostic system 10. In some embodiments, the external fixture 300 includes components 450 configured to act as a stabilizing platform to orient the system 10 in a (e.g., horizontal, vertical, etc.) position during analysis, and includes one or more stabilizers configured to hold the system 10 during mechanical operation of the pumps and/or other components of the system 10. In some embodiments, the external fixture 300 may include specific components in specific locations that correspond to specific locations on the chip body. For example, a piezoelectric transducer (PZT) may be included in and/or held by the external fixture 300 in a position that corresponds to the mixing chamber 14, attachment of electrodes to the external fixture 300 for electrochemical pumping (e.g., operation of the first pump 18) may be made in a location that corresponds to the first pump 18, and one or more heating strips may be placed in one or more locations that correspond to the first and second valves 28 and 26. In addition, mechanical compressors 450 may be included in and/or held by the external fixture 300 in positions that align with the reagent-storing blisters 31 and 33 when the chip body 12 is placed in and/or on the external fixture 300. Continuing with this example, the external fixture 300 may be configured such that one or more primary mechanical compressors 450 control the compression of the smaller blisters 35 and 37 (FIG. 1), which when compressed, contact the ball, for the initial opening of the blister. In some embodiments, the external fixture 300 may be configured such that two secondary compressors 450 contact the larger subsection 36 and 38 (FIG. 1) of the blisters for the pumping of the reagents and solutions into the main channel 16.

In some embodiments, attachable motors 400 (as described above) may be configured to work in compatibility with the compressors 450 located on the fixture 300 for the control of compression, and thus speed of flow. These motors 400 may be controlled with attached printed circuit board (PCB) 402 motors with buttons for autonomous and/or controlled operation, for example.

FIGS. 5A and 5B illustrate an example of normally closed valve 26 that leads to amplification chamber 24. FIG. 5A illustrates valve 26 in a closed position and FIG. 5B illustrates valve 26 in an open position. Normally closed valve 26 leading to the amplification chamber 24 begins in the diagnostic process (e.g., as described above) in a closed configuration (FIG. 5A), as separated waste components will be separated accordingly. However, to successfully transfer the amplification reagents and enzymes with separated targets to the amplification chamber 24 for analysis, the amplification chamber valve 26 must open (FIG. 5B), while the opposite valve (e.g., 28 shown in FIG. 1) closes. Heat is applied through the resistive heating strip (described above), melting the solidified wax 500. The pump (e.g., 18 or A shown in FIG. 1 or 2) pushes the wax 500 further into 502 a valve channel 504, in which surface tension causes the melted wax 500 to flow on the surface 506 of a wider portion 508 channel, in turn, opening the path toward the amplification chamber 24 (FIG. 5B).

Figure 6B:
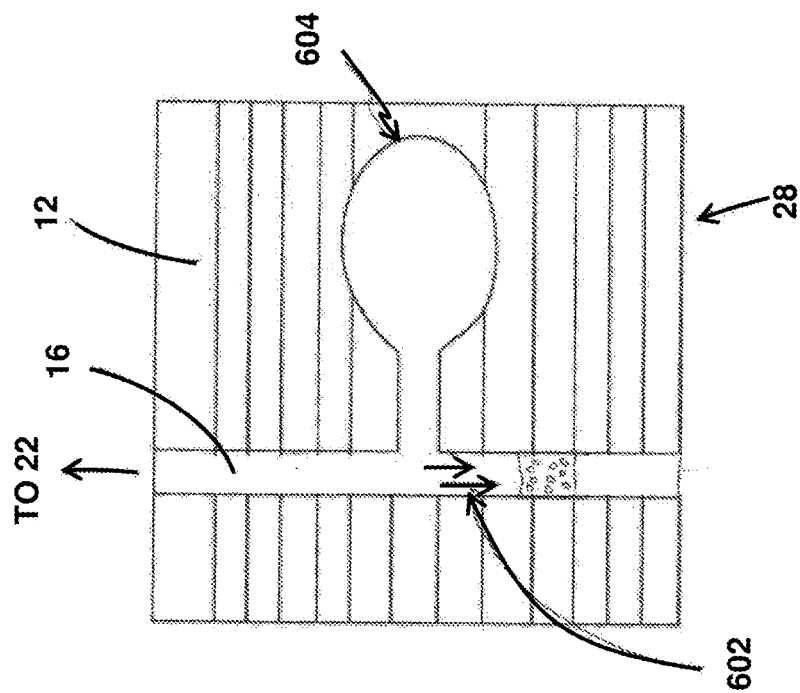
FIG. 6B illustrates the different valve that leads to the waste chamber in a closed position.
Figure 6A:
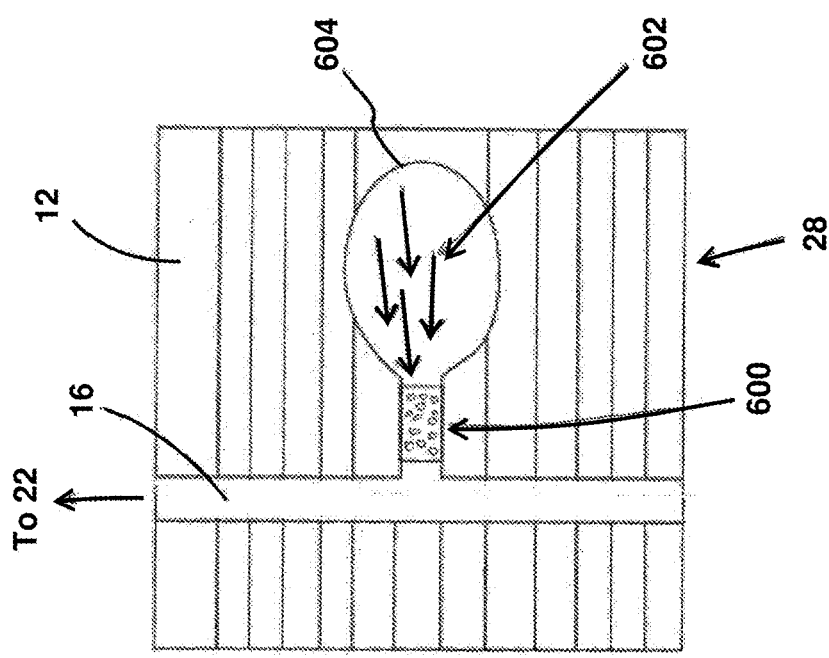
FIG. 6A illustrates a different valve that leads to a waste chamber in an open position.

FIGS. 6A and 6B illustrate normally open valve 28 that leads to the waste chamber 22 (FIG. 1). In contrast to the amplification chamber 24 valve 26, the normally open valve 28 leading to the waste chamber 22 starts out in the diagnostic process as open (FIG. 5A), to facilitate transportation of separated waste to the waste chamber 22 (e.g., as described above). To close the valve 28 for transportation of RNA targets and amplification reagents and enzymes to the amplification chamber 24 (FIG. 1), the adhesive resistive heater (described above) is applied to melt the wax 600. Air 602 in the valve 28 chamber 604 expands when heated, pushing the wax 600 into the main channel 16, in which it solidifies and closes the main channel 16 (FIG. 6B).

Figure 7B:
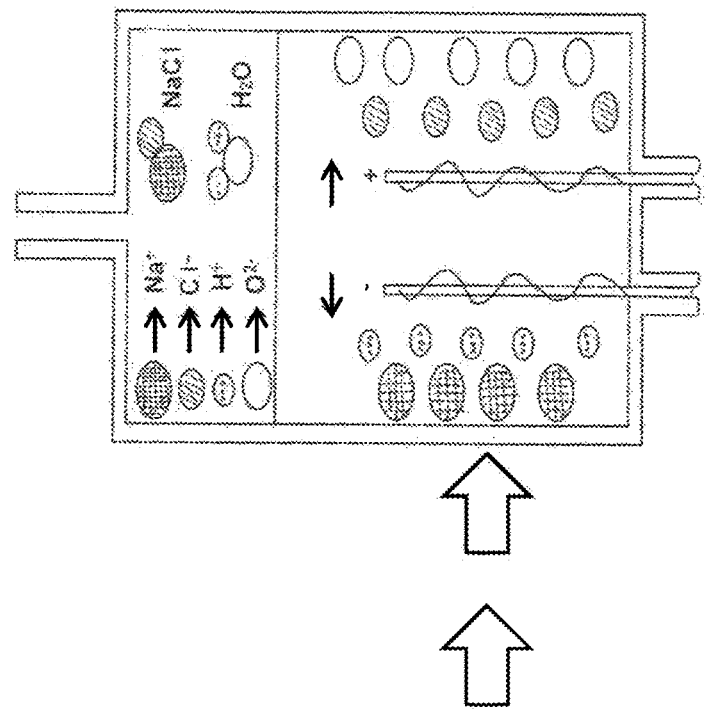
FIG. 7B is a diagram of a second corresponding portion of the water electrolysis process.
Figure 7A:
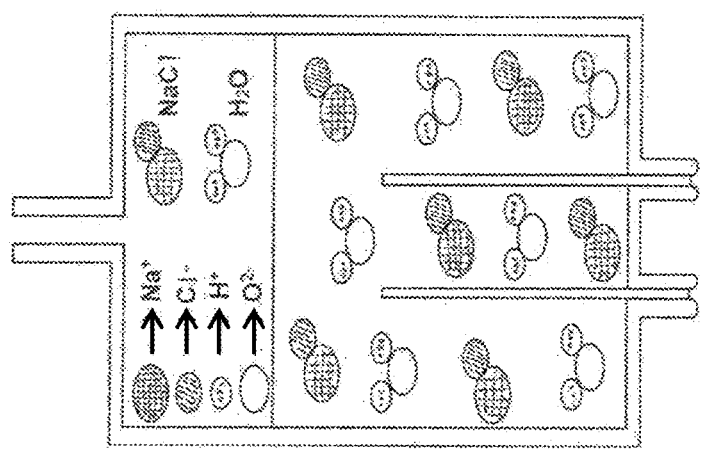
FIG. 7A is a diagram of a first portion of a water electrolysis process for micro pumping.

FIGS. 7A and 7B combine to form a diagram of a water electrolysis process for micro pumping (e.g., a process performed by pump 18 and/or other pumps described above. Micro pumping was primarily based on an electrochemical decomposition reaction (electrolysis) of water in a sodium chloride solution. The reduction of sodium ions in this reaction is thermodynamically very difficult, and water is reduced, evolving hydrogen molecules and leaving hydroxide ions in the resulting solution. At the anode, the oxidation of chlorine is occurs rather than the oxidation of water since the over potential for the oxidation of sodium chloride to chlorine is lower than the over potential for the oxidation of water to oxygen. Based on this information, system 10 is configured such that the use of sodium chloride significantly suppresses oxygen gas production, effectively regulates pumping functions, and eliminates safety risks associated with electrolysis-based pumping. As shown in FIGS. 7A and 7B, the hydroxide ions and dissolved chlorine gas react further to form hypochlorous acid. As shown in the transition of from FIG. 7A to FIG. 7B, the application of DC current to the sodium chloride solution instigates a decomposition reaction, creating two oppositely charged poles, the anode and cathode. This separation of the ionic bonds leads to production of new chemical compounds and molecules including hydrogen gas for pumping and sodium hypochlorite.

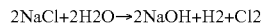

$$2NaCl + 2H_2O \rightarrow 2NaOH + H_2 + Cl_2$$

The equation above describes the chemical reaction that may take place. Oxidation takes place at the anode (oxygen and chlorine ions), while reduction takes place at the cathode (release of hydrogen gas). The separation of ionic compounds creates further chemical activity with resulting molecule exposures (i.e. chlorine and sodium hydroxide ions).

Figures 8A, 8B:
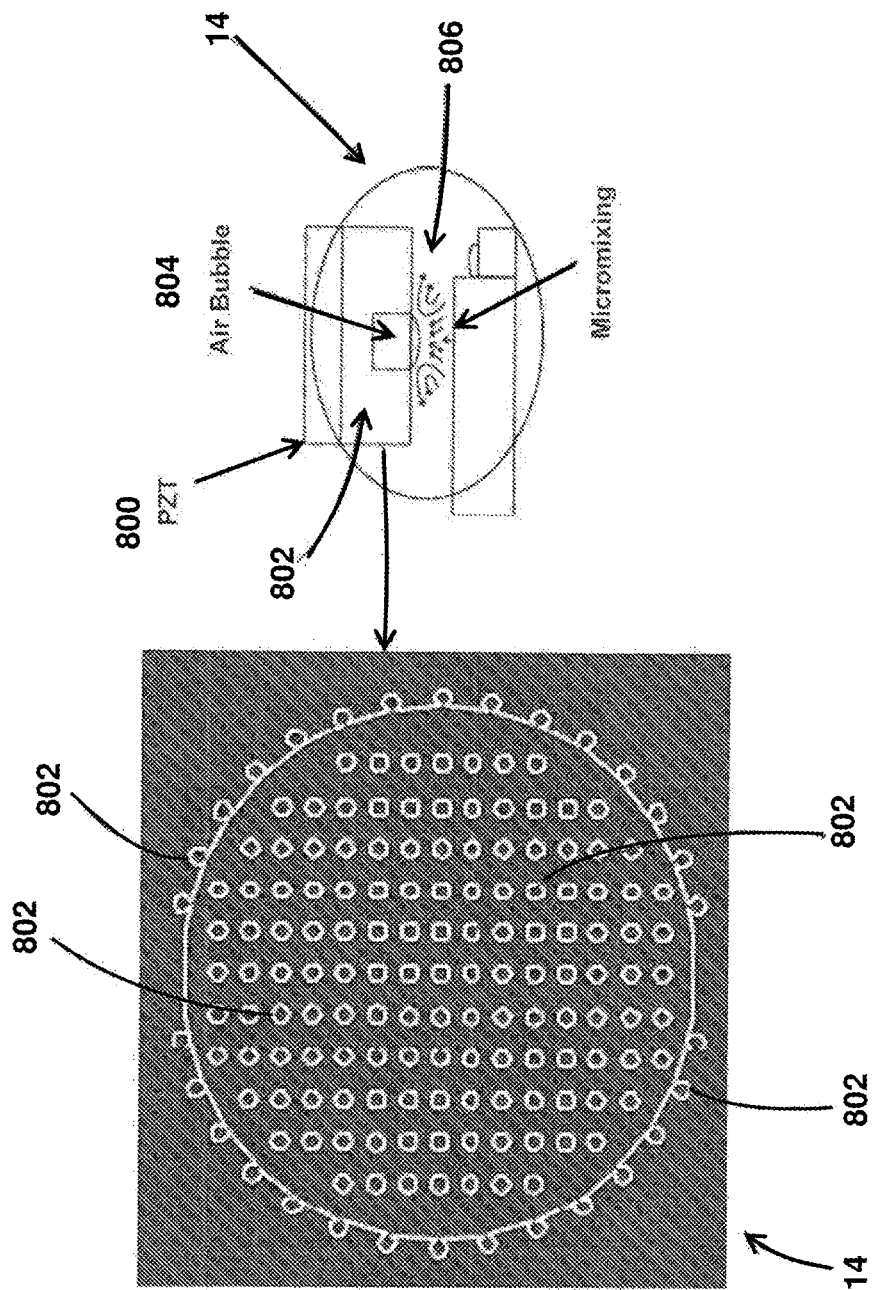
FIG. 8A illustrates a top view of a mixing chamber.
FIG. 8B illustrates a cross section view of the mixing chamber.

FIG. 8A illustrates a top view of mixing chamber 14. FIG. 8B illustrates a cross section view of mixing chamber 14. FIGS. 8A and 8B illustrate mixing chamber 14 with air pockets/cavities. Acoustic-enhanced micro mixing is based on the use of acoustic energy resonating in air interfaces to manipulate particle motion through acoustic incident waves, and in turn, enhance mixing of solutions with self-containment, as in chamber 14. This facilitates sample preparation and RNA magnetic separation, and yet is simple and effective. Acoustic energy created by a function generator (e.g., included in and/or coupled to external fixture 300 described in FIGS. 3 and 4) is transferred into a PZT disk 800 (FIG. 8B), which spreads acoustic vibrations (at a controlled frequency) to the mixing chamber 14. PZT disk 800 (FIG. 8B) may be included in and/or coupled to external fixture 300 (described in FIGS. 3 and 4), coupled to chip body 12 (FIG. 1) on a "top" or "bottom" side (e.g., either side of chip body 12) of chamber 14, and/or be located in other positions. Within the lateral cavities 802, small air pockets form because fluid surface tension traps air within the cavities 802. When exposed to acoustic vibrations, these air pockets or bubbles 804 vibrate rapidly. At the resonance frequency, these air bubbles 804 produce acoustic incident waves 806. The chamber 14 is configured to encompass close proximity between cavities/pockets 802 for rapid reflection of waves 806, hence more efficient macromixing. Various relationships between cavity design elements (i.e., depth, width, diameter, etc.) and mixing efficiencies are contemplated.

Figure 9:
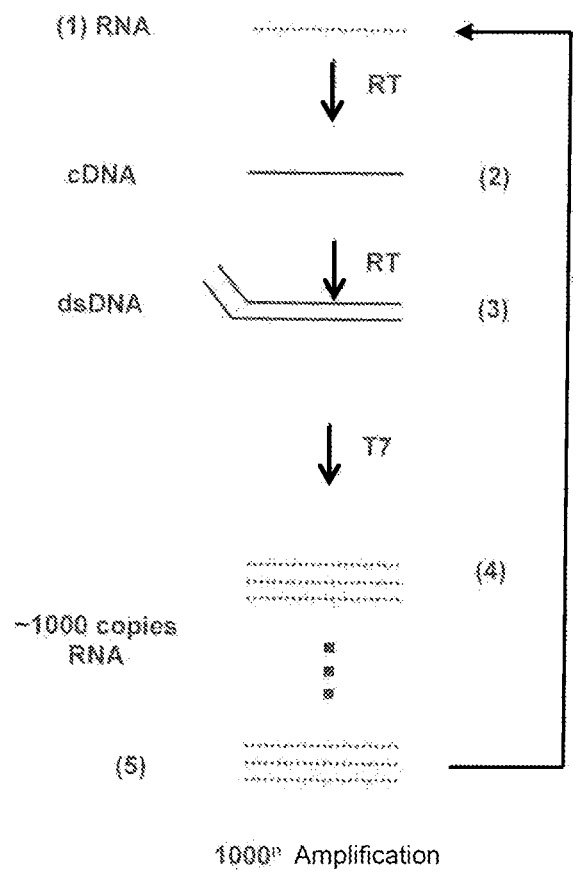
FIG. 9 illustrates isothermal transcription mediated amplification.

FIG. 9 illustrates isothermal transcription mediated amplification. FIG. 9 is a diagram illustrating an isothermal transcription-mediated amplification process that may be performed with system 10 in which RNA amplification reagents and enzymes amplify RNA targets for fluorescent analysis. A CT (for example) assay carried out with system 10 may be based on an RNA amplification technique called transcription mediated amplification (TMA). During this process, reverse transcriptase, using a bound T7 primer creates a complimentary DNA strand to its original RNA target, erases the original RNA strand, and copies the resulting DNA strand to form a cDNA double-strand, that serves as a template for RNA amplification. T7 RNA transcriptase initiates transcription on the cDNA template, creating several hundreds of copies of RNA amplicons. Single-stranded nucleic acid torches with fluorophores and quenchers bind to the RNA amplicons, and through excitement, fluoresce, creating a signal to display fluorescent intensity. The generated fluorescent intensity is measured in representation of RNA targets captured and amplified. Intensity directly corresponds to level of target capturing.

Although the system(s) or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:
1. A disease diagnostic system, the system comprising:
a generally rectangular chip body having two longer sides and two shorter sides with a main channel starting on and running along a first long side of the chip body, turning and running along a first short side of the chip body, and turning again and running along a second long side of the chip body, the second long side of the chip body opposite the first long side of the chip body;

a mixing chamber formed in the chip body along the main channel, the mixing chamber formed toward the first long side of the chip body, the mixing chamber configured to receive a biological sample for disease diagnosis, the mixing chamber comprising a plurality of lateral cavities in proximity to each other, magnetic beads, and a cell lysis buffer, the mixing chamber configured to receive energy to facilitate mixing in the mixing chamber to form a solution, wherein fluid surface tension traps air within the plurality of lateral cavities such that, when the energy is received, the trapped air vibrates rapidly at a resonance frequency and produces acoustic incident waves, and wherein the proximity of the plurality of lateral cavities causes rapid reflection of the acoustic incident waves in the mixing chamber;

a first pump formed in the chip body upstream from the mixing chamber and toward the first long side of the chip body, and coupled to the mixing chamber, the first pump configured to pump the solution out of the mixing chamber;

the main channel formed in the chip body and coupled to the mixing chamber, the main channel configured to receive the solution pumped from the mixing chamber;

a separation area formed in the main channel downstream from the mixing chamber and the first pump, the separation area formed toward the first short side of the chip body, the separation area configured to receive a magnet that traps the magnetic beads and ribonucleic acid (RNA) and/or deoxyribonucleic acid (DNA) molecules in the solution bound to the magnetic beads on a surface of the separation area;

a waste chamber formed in the chip body coupled to the main channel downstream from the separation area at a termination of the main channel, the waste chamber formed toward the second long side of the chip body, the waste chamber configured to receive solution comprising unbound RNA and/or DNA molecules;

a first valve positioned between the main channel and the waste chamber downstream from the separation area and toward the first short side of the chip body, the first valve configured to control flow of the solution comprising the unbound RNA and/or DNA molecules through the main channel to the waste chamber;

an amplification chamber formed in the chip body toward the first short side and the second long side of the chip body, the amplification chamber coupled to the main channel downstream from the separation area by a side channel, the amplification chamber configured to receive the bound RNA and/or DNA molecules for analysis;

a second valve positioned between the main channel and the amplification chamber along the side channel and configured to control flow of the bound RNA and/or DNA molecules through the main channel and the side channel to the amplification chamber;

a second pump formed in the chip body toward the first long side of the chip body and coupled to the main channel between the mixing chamber and the separation area, the second pump coupled to a cavity holding a wash buffer solution; and a third pump formed in the chip body toward the first long side of the chip body and coupled to the main channel between the second pump and the separation area, the third pump coupled to a cavity holding amplification solution;

wherein:
with the first and second valves in a first configuration that allows flow through the main channel to the waste chamber and blocks flow to the amplification chamber, and with the bound RNA and/or DNA molecules trapped in the separation area, activation of the second pump pumps the wash buffer solution and the solution comprising the unbound RNA and/or DNA molecules through the main channel into the waste chamber; and with the first and second valves in a second configuration that allows flow through the main channel to the amplification chamber and blocks flow to the waste chamber, and with the bound RNA and/or DNA molecules released from the separation area, actuation of the third pump pumps the amplification solution and the bound RNA and/or DNA molecules through the main channel into the amplification chamber.

2. The system of claim 1, wherein the plurality of lateral cavities in the mixing chamber are configured to trap air bubbles when fluid is loaded into the mixing chamber, the air bubbles configured to function as mechanical actuators during mixing in the mixing chamber.

3. The system of claim 2, wherein the mixing chamber is configured to receive external energy from a piezoelectric transducer (PZT) such that vibrations are transferred from the PZT to the mixing chamber and cause the air bubbles to oscillate and produce the acoustic incident waves in the mixing chamber to cause the RNA and/or DNA molecules to couple with the magnetic beads.

4. The system of claim 1, wherein the first pump comprises an electrochemical decomposition reaction (electrolysis) of water in a sodium chloride solution.

5. The system of claim 1, wherein the second pump comprises a first blister formed in the chip body, the first blister configured to be actuated by a first mechanical external force.

6. The system of claim 1, wherein the third pump comprises a second blister formed in the chip body, the second blister configured to be actuated by a second mechanical external force.

7. The system of claim 1, wherein the first valve and the second valve are wax valves.

8. The system of claim 7, wherein the first valve and the second valve are actuated by one or more heat sources coupled to a surface of the chip body at or near the first valve and the second valve.

9. The system of claim 1, wherein the solution comprises only RNA molecules bound to the magnetic beads, and wherein the amplification chamber is configured to facilitate:
amplification using transcription-mediated amplification; and
analysis for fluorescent signals with a real-time polymerase chain reaction.

10. The system of claim 1, wherein the system further comprises an external fixture configured to:
receive the chip body and removably couple with the chip body to retain the chip body in a predetermined orientation with respect to the external fixture;
actuate a piezoelectric transducer (PZT), wherein the mixing chamber further comprises one or more cavities configured to trap air bubbles when fluid is loaded into the mixing chamber, the air bubbles configured to function as mechanical actuators during mixing in the mixing chamber, and wherein the mixing chamber is configured to receive external energy from the PZT such that vibrations are transferred from the PZT to the mixing chamber and cause the air bubbles to oscillate and produce acoustic incident waves in the mixing chamber to cause the RNA and/or DNA molecules to couple with the magnetic beads;

activate the first pump;

trap and untrap the bound RNA and/or DNA molecules;

actuate the first and second valves to cause the system to change from the first configuration to the second configuration, and actuate the second and third pumps.

11. A disease diagnosis method performed with the disease diagnostic system of claim 1, the method comprising:

forming the generally rectangular chip body with the main channel;

forming the mixing chamber in the chip body along the main channel, the mixing chamber configured to receive the biological sample for disease diagnosis, the mixing chamber comprising the plurality of cavities, the magnetic beads, and the cell lysis buffer;

causing the mixing chamber to receive the energy to facilitate mixing in the mixing chamber to form the solution, wherein the fluid surface tension traps air within the plurality of lateral cavities such that, when the energy is received, the trapped air vibrates rapidly at the resonance frequency and produces the acoustic incident waves, and wherein the proximity of the plurality of lateral cavities causes the rapid reflection of the acoustic incident waves in the mixing chamber;

forming the first pump in the chip body upstream from the mixing chamber, coupling the first pump to the mixing chamber, and pumping the solution out of the mixing chamber with the first pump;

coupling the main channel to the mixing chamber, and receiving the solution pumped from the mixing chamber with the main channel;

forming the separation area in the main channel downstream from the mixing chamber and the first pump, the separation area formed toward the first short side of the chip body, and receiving the magnet that traps the magnetically bound ribonucleic acid (RNA) and/or deoxyribonucleic acid (DNA) molecules in the solution on a surface of the separation area;

forming the waste chamber in the chip body at a termination of the main channel, the waste chamber formed toward the second long side of the chip body, coupling the waste chamber to the main channel downstream from the separation area, and receiving the solution comprising unbound RNA and/or DNA molecules with the waste chamber;

positioning the first valve between the main channel and the waste chamber to control the flow of the solution comprising the unbound RNA and/or DNA molecules through the main channel to the waste chamber;

forming the amplification chamber in the chip body, coupling the amplification chamber to the main channel downstream from the separation area, and receiving the bound RNA and/or DNA molecules for analysis with the amplification chamber;

positioning the second valve between the main channel and the amplification chamber to control the flow of the bound RNA and/or DNA molecules through the main channel to the amplification chamber;

forming the second pump in the chip body and coupling the second pump to the main channel and a cavity holding the wash buffer solution;

forming the third pump in the chip body and coupling the third pump to the main channel and a cavity holding amplification solution;

with the first and second valves in the first configuration that allows flow through the main channel to the waste chamber and blocks flow to the amplification chamber, and with the bound RNA and/or DNA molecules trapped in the separation area, actuating the second pump to pump the wash buffer solution and the solution comprising the unbound RNA and/or DNA molecules through the main channel into the waste chamber; and with the first and second valves in the second configuration that allows flow through the main channel to the amplification chamber and blocks flow to the waste chamber, and with the bound RNA and/or DNA molecules released from the separation area, actuating the third pump to pump the amplification solution and the bound RNA and/or DNA molecules through the main channel into the amplification chamber.

12. The method of claim 11, wherein the plurality of lateral cavities in the mixing chamber are configured to trap air bubbles when fluid is loaded into the mixing chamber, the air bubbles configured to function as mechanical actuators during mixing in the mixing chamber.

13. The method of claim 12, further comprising receiving, with the mixing chamber, external energy from a piezoelectric transducer (PZT) such that vibrations are transferred from the PZT to the mixing chamber and cause the air bubbles to oscillate and produce the acoustic incident waves in the mixing chamber to cause the RNA and/or DNA molecules to couple with the magnetic beads.

14. The method of claim 11, wherein the first pump comprises an electrochemical decomposition reaction (electrolysis) of water in a sodium chloride solution.

15. The method of claim 11, wherein the second pump comprises a first blister formed in the chip body, the method further comprising actuating the first blister with a first mechanical external force.

16. The method of claim 11, wherein the third pump comprises a second blister formed in the chip body, the method further comprising actuating the second blister with a second mechanical external force.

17. The method of claim 11, wherein the first valve and the second valve are wax valves.

18. The method of claim 17, further comprising actuating the first valve and the second valve with one or more heat sources coupled to a surface of the chip body at or near the first valve and the second valve.

19. The method of claim 11, wherein the solution comprises only RNA molecules bound to the magnetic beads, the method further comprising facilitating, with the amplification chamber:

amplification using transcription-mediated amplification; and analysis for fluorescent signals with a real-time polymerase chain reaction.

20. The method of claim 11, wherein the system further comprises an external fixture, the method further comprising:

receiving, with the external fixture, the chip body and removably coupling with the chip body to retain the chip body in a predetermined orientation with respect to the external fixture;

actuating, with the external fixture, a piezoelectric transducer (PZT), wherein the mixing chamber further comprises one or more cavities configured to trap air bubbles when fluid is loaded into the mixing chamber, the air bubbles configured to function as mechanical actuators during mixing in the mixing chamber, and wherein the mixing chamber is configured to receive external energy from the PZT such that vibrations are transferred from the PZT to the mixing chamber and cause the air bubbles to oscillate and produce acoustic incident waves in the mixing chamber to cause the RNA and/or DNA molecules to couple with the magnetic beads;

activating, with the external fixture, the first pump;

trapping and untrapping, with the external fixture, the bound RNA and/or DNA molecules;

actuating, with the external fixture, the first and second valves to cause the system to change from the first configuration to the second configuration, and actuating, with the external fixture, the second and third pumps.

\* \* \* \* \*